United States Patent [19]

Gogolewski et al.

[11] Patent Number: 4,915,893
[45] Date of Patent: Apr. 10, 1990

[54] METHOD OF PREPARING POLYESTER FILAMENT MATERIAL

[75] Inventors: Sylwester Gogolewski, Renens, Switzerland; Albert J. Pennings, Norg, Netherlands

[73] Assignee: Medtronic, Inc., Minneapolis, Minn.

[21] Appl. No.: 597,159

[22] PCT Filed: Jul. 15, 1983

[86] PCT No.: PCT/NL83/00028

§ 371 Date: Mar. 13, 1984

§ 102(e) Date: Mar. 13, 1984

[87] PCT Pub. No.: WO84/00303

PCT Pub. Date: Feb. 2, 1984

[30] Foreign Application Priority Data

Jul. 16, 1982 [NL] Netherlands .................. 8202894

[51] Int. Cl.⁴ .............................................. D01F 1/02
[52] U.S. Cl. .................. 264/205; 264/210.6; 264/211; 264/211.14
[58] Field of Search ........... 525/28, 440, 444, 455, 525/460; 264/210.8, 211.17, 210.6, 211.14, 211, 205

[56] References Cited

U.S. PATENT DOCUMENTS

| | | |
|---|---|---|
| 2,127,903 | 8/1938 | Bowen . |
| 2,836,181 | 5/1958 | Tapp . |
| 2,861,319 | 11/1958 | Breen ............................. 264/171 |
| 2,933,478 | 4/1960 | Young et al. ................... 525/440 |
| 2,962,470 | 11/1960 | Jung ............................... 525/440 |
| 2,990,605 | 7/1961 | Demsyk . |
| 3,044,942 | 7/1962 | Baptist . |
| 3,054,406 | 9/1962 | Usher . |
| 3,096,560 | 7/1963 | Liebig . |
| 3,105,492 | 10/1963 | Jeckel . |
| 3,108,357 | 10/1963 | Liebig . |
| 3,117,906 | 1/1964 | Tonner ........................... 264/171 |
| 3,124,136 | 3/1964 | Usher . |
| 3,142,067 | 7/1964 | Liebig . |
| 3,155,095 | 11/1964 | Brown . |
| 3,176,316 | 4/1965 | Bodell . |
| 3,272,204 | 9/1966 | Artandi et al. . |
| 3,276,448 | 10/1966 | Kronenthal . |
| 3,304,557 | 2/1967 | Polansky . |
| 3,316,557 | 5/1967 | Liebig . |
| 3,317,924 | 5/1967 | LeVeen . |
| 3,331,814 | 7/1967 | Randall . |
| 3,366,440 | 1/1968 | Nuwayser . |
| 3,371,069 | 2/1968 | Miyamae et al. . |
| 3,376,869 | 4/1968 | Borysko . |
| 3,400,719 | 9/1968 | Buddecke . |
| 3,408,659 | 11/1968 | Thiele et al. . |
| 3,425,418 | 2/1969 | Chvapil et al. . |
| 3,512,183 | 5/1970 | Sharp . |
| 3,585,647 | 6/1971 | Gajewski . |
| 3,636,956 | 1/1972 | Schneider . |
| 3,739,773 | 6/1973 | Schmitt . |
| 3,797,499 | 3/1974 | Schneider . |
| 3,853,462 | 12/1974 | Smith . |
| 3,875,937 | 4/1975 | Schmitt . |
| 3,883,901 | 5/1975 | Coquard et al. . |
| 3,886,947 | 6/1975 | Sawyer . |
| 3,894,530 | 7/1975 | Dardik et al. . |
| 3,908,201 | 9/1975 | Jones et al. . |
| 3,933,728 | 1/1976 | Henbest ........................... 525/28 |
| 3,966,866 | 6/1976 | Ballman et al. ................. 264/171 |
| 3,974,526 | 8/1976 | Dardik et al. . |

(List continued on next page.)

OTHER PUBLICATIONS

Annis et al., article entitled "An Elastomeric Vascular Prosthesis," vol. XXIV, Trans. Am. Soc. Artif. Intern. Organs, 1978, p. 209.

Andrade et al., article entitled "Blood-Materials Interactions—20 Years of Frustration," vol. XXVII, Trans. Am. Soc. Artif. Intern. Organs, 1981, p. 659.

Comment entitled "Experimental Study of a New Synthetic Vascular Graft", by Gruss et al., at page 518, J. Cardiovas. Surg., 22, 1981, of the IX World Congress of the International Cardiovascular Society.

Primary Examiner—Hubert C. Lorin
Attorney, Agent, or Firm—Vidas & Arrett

[57] ABSTRACT

Method of preparing a new synthetic surgical filament material by spinning a mixture of a polyester and an additive.

11 Claims, 1 Drawing Sheet

U.S. PATENT DOCUMENTS

| | | |
|---|---|---|
| 4,086,203 | 4/1978 | Shaw et al. ............................ 525/28 |
| 4,127,124 | 11/1978 | Clagett . |
| 4,140,678 | 2/1979 | Shalaby et al. . |
| 4,141,087 | 2/1979 | Shalaby et al. . |
| 4,156,067 | 5/1979 | Gould . |
| 4,164,045 | 8/1979 | Bokros . |
| 4,171,087 | 10/1979 | Kunz . |
| 4,187,852 | 2/1980 | Urry et al. . |
| 4,205,399 | 6/1980 | Shalaby et al. . |
| 4,208,511 | 6/1980 | Shalaby et al. . |
| 4,209,607 | 6/1980 | Shalaby et al. . |
| 4,224,946 | 9/1980 | Kaplan . |
| 4,242,488 | 12/1980 | Stanley et al. . |
| 4,243,775 | 1/1981 | Rosensaft et al. . |
| 4,246,904 | 1/1981 | Kaplan . |
| 4,271,070 | 6/1981 | Miyata et al. . |
| 4,300,244 | 11/1981 | Bokros . |
| 4,300,565 | 11/1981 | Rosensaft et al. . |
| 4,314,561 | 2/1982 | Kaplan . |
| 4,316,457 | 2/1982 | Liegeois . |
| 4,323,525 | 4/1982 | Bornat . |
| 4,343,931 | 8/1982 | Barrows . |
| 4,355,426 | 10/1982 | MacGregor . |
| 4,408,023 | 10/1983 | Gould et al. ........................ 525/455 |
| 4,413,072 | 11/1983 | Hess et al. ............................ 525/28 |
| 4,416,028 | 11/1983 | Eriksson et al. . |
| 4,424,305 | 1/1984 | Gould et al. ........................ 525/455 |
| 4,448,936 | 5/1984 | Wang et al. ........................ 525/440 |

*Fig. 1* *Fig. 2* *Fig. 3* *Fig. 4*
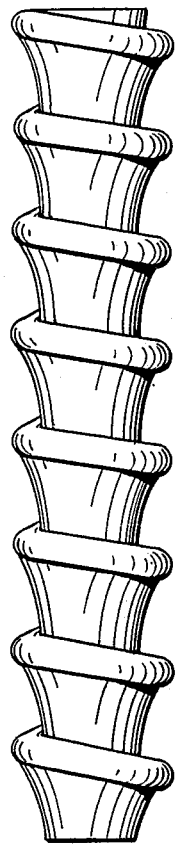   

METHOD OF PREPARING POLYESTER FILAMENT MATERIAL

This invention relates to a process for the manufacture of a polyester comprising filament material suitable for surgical application, as such or in woven, braided or knitted form, as well as reinforcing beads. The invention further relates to a synthetic surgical material that is biocompatible with a patient and is biodegradable.

The invented process of spinning a polyester material in the presence of a certain additive can be used in the production of highly fibrillated sutures, which due to their fibrillation exhibit a good resorption rate and flexibility important for handling the suture and tying the knot.

Regular structurization at the fibre surface, created in the present spinningprocess, and preserved in the fibre even after hotdrawing, provides to the fibre a high knot strength.

There exist a number of commercial biocompatible and biodegradable sutures based on polyglycolide (Dexon), copolymer of lactide and glycolide (Vicryl), or lactone of hydroxyethyl glycolic acid (PDS). These well known materials are convenient to handle, and have the required rate of bioresorption. However there still exists a need for new biocompatible and biodegradable suture materials.

As follows from literature data, polylactide fibers have already been produced, but the rate of degradation of these fibers is too low as compared with that of Vicryl, Dexon or PDS sutures.

While Vicryl, Dexon and PDS sutures respectively disappear after about 90, 120 and 180 days from implantation, the polylactide sutures are not resorbed until after about 8 to 17 months from implantation.

Thus although polylactide is a biocompatible, biodegradable and fiberforming polymer, the polylactide sutures have not so far found practical application in surgery.

It is an object of the present invention to provide sutures with adequate tensile strength, high dimensional stability and a rate of hydrolysis comparable to those of Vicryl, Dexon or PDS sutures. It is another object of the present invention to provide fibers which have a flexibility higher than those produced according to the standard methods, yet having high tensile strength and modulus. It is a further object of the present invention to provide sutures having a knot strength higher than that of fibers produced by standard spinning procedures.

These and other objects are attained by filament material produced by dry- or wet-spinning a spinning mixture comprising a polyester material and an additive, particularly a polyurethane material. When wet-spinning a coagulant material is needed. Preferred polyester materials are poly (L-lactide), (PLLA), poly (DL-LACTIDE) (PDLLA), and combinations thereof, having a viscosity-average molecular weight of at least about $3 \times 10^5$ and preferably above $5.0 \times 10^5$ Kg/kmol, as calculated according to the formule: $[\eta] = 5.45 \times 10^{-4} M_v^{0.73}$, for a viscosity measured at 25° C. in trichlormethane.

Examples of additives other than polyurethane materials which can be used in preparing the filament material of this invention, are glycolide, lactide, camphor, benzoic acid-2-hydroxyacetate, hexamethylbenzene, 1,2-cyclohexandione and other low-molecular weight organic compounds which are preferably soluble in trichlormethane and/or dichlormethane and ethanol, and have a melting temperature in the range of 40° to 180° C.

Polyurethane is a preferred additive in the spinning mixture, and as such may be used in the form of a polyester urethane based on hexamethylene diisocyanate, 1,4-butanediol and a copolymer of lactic acid and ethylene glycol, diethylene glycol or tetramethylene glycol; hexamethylene diisocyanate, 2,4,6-tris(dimethylaminomethyl)phenol and copolymer of lactic acid and diethylene glycol, ethylene glycol, or tetramethylene glycol, a polyester urethane based on hexamethylene diisocyanate, trimethylol propane and a copolymer of polylactic acid and tetramethylene glycol or a polyester urethane based on 4,4'-diphenylmethane diisocyanate, 1,4-butanediol and polytetramethylene adipate. The concentration of the additive in the polylactide material may be in the range of 1 to 45% by weight.

Filament material prepared from these kinds of polylactide/additive mixtures may be formed by dry-spinning the polymer/additive mixture from a solution in a good solvent, in particular in dichloromethane and/or trichloromethane at room temperature through a spinneret. The filament material obtained in thereafter, according to a particularly preferred embodiment of the process according to the invention, subjected to a hotdrawing operation applying a drawing ratio within a wide range, particularly up to about 25.

The resulting oriented filaments are strong and owing to their regularly structurized surface form strong knots.

Owing to extensive fibrillation by virtue of using an additive, the fibres are flexible and easy to handle upon suturing or knotting and hydrolyse much faster than the standard polylactide fibers.

The invented fibers, such as the polylactide comprising fibers, exhibit very little shrinkage when heated at 37° C. in water for 30 hours, namely, about 1 to 5 percent of their initial length. The invented spinning process avoids degradation of the polymer during extrusion, resulting in fibers of higher tensile strength.

It is recommended that ethylene oxide be applied for sterilization of the fibers, for example polylactide comprising fibers, as high-energy radiation may result in crosslinking and chain scission and some decrease in tensile strength.

After sterilization with ethylene oxide, the sutures in sealed packages, are subjected to a vacuum of $10^{-4}$ Torr at 70° C. for 1 hour. This avoids absorption of sterilizing gas in the sutures.

The filaments according to the present invention have a good tensile strength of at least 0.4GPa, preferably 0.7 GPA. Some have tensile strengths as high as 0.8 to 1.0 GPa. The invented fibers are resorbed as to 50% after about 150 days, which rate of hydrolysis is comparable to that of PDS fibers with comparable thickness and strength.

The filaments according to the invention, such as the polylactide comprising fibers, may be woven, braided, knitted or used as monofilaments of general surgical application, may be used as reinforcing beads for the construction of biodegradable tracheal or vascular prostheses, especially for by-pass systems. The polymeric additive material, in particular when being PLLA and/or PDLLA, which can be converted to filaments particularly by dry-spinning, may be present in a spinning solution, and this in a concentration of 10 to 40% by weight in dichloromethane and/or trichloromethane, as these two solvents easily dissolve the polylactide/additive mixture with the above viscosity-average molecular weight of about $3 \times 10^5$ Kg/kmol at room temperature. Spinning polylactide/additive fibers from a solution with a concentration in the range of 10 to 40% by weight provides a monofilament of reasonable tensile strength, which is in addition regularly structurized due to the melt fracture as schematically shown in the accompanying drawing as obtained (drawing ratio $\lambda = 0$) and after hot-drawing at drawing ratios $\lambda$ of 6, 10 and 20, respectively. Even hot-drawing at high draw ratios does not completely remove the surface structure but results in an extension of the pitch of the helix structure.

The diameter of the resulting fibre will generally be in the range of 0.3 to $1 \times 10^{-4}$ m. Preferred monofilaments have a diameter of about 0.4 to $1 \times 10^{-4}$ m.

Spinnerets having orifice sizes of 0.2 to 1 mm and a length of the capillary of 10 mm are suitable for spinning the monofilaments. In dry-spinning from dichlormethane or trichlormethane solutions, the solution is extruded at room temperature at which the solvent evaporates slowly. A preferred polymer/additive concentration is 15–25, in particular about 20% by weight.

The filament is extruded at a speed in the range of 0.02 to 2 mm/min. This gives no orientation to the fibre as spun. After spinning the polylactide fibers are hot-drawn at a temperature in the range of 45° to 200° C., preferably at 110°, 170°, 180° or 200° C., which temperature depends on the additive concentration in the polymer and the melting temperature of the additive.

The draw ratio $\lambda$ may be up to 25, preferably 14 to 18. Take-up speed may be in the range of 0.2 to 1 cm.sec$^{-1}$ with a strain rate in the range of $10^{-3}$ sec.

The hot-drawing of fibers may be carried out in an electric tube-furnace with a length of 60 cm under a dry, oxygen-free atmosphere. Hot-drawing at temperatures above 120° C. may reduce the molecular weight of the starting polymer by 1–2 percent.

The filament can be colored by adding an inert material, e.g. Cosmetic Violet No. 2, to the solvent before preparation of the spinning solution.

The invention is illustrated in and by the following examples II, III and IV, example I being included for comparison purposes:

EXAMPLE I

Filaments with a regularly structurized surface and having a diameter of $0.44 \times 10^{-4}$ m, a tensile strength of 1 GPa, a modulus of 12 GPa, a strength of square knot of 0.6 GPa and an elongation at break of 18% were prepared by spinning poly (L-lactide) from a 20 wt % solution in trichloromethane at room temperature.

The poly(L-lactide) had a viscosity-average molecular weight of $6.0 \times 10^5$. The fibre as spun was hot-drawn at 200° C. to a draw ratio of 20.

EXAMPLE II

Filaments with a regularly structurized surface and having a diameter of $0.6 \times 10^{-4}$ m, a tensile strength of 0.8 GPa, a modulus of 9 GPa, a strength of a square knot of 0.5 GPa and an elongation at break of 17% were prepared by spinning poly(L-lactide) which contained 10% by weight of camphor, from a 20 wt % solution in trichloromethane at room temperature. The poly(L-lactide) had a viscosity-average molecular weight of $6.0 \times 10^5$. The fibre was drawn at 180° C. to a draw ratio of 4.

After hot-drawing the filaments were extracted in ethanol for 4 hours. No additive was present in the fibre after extraction. The filaments obtained turned out to have a highly fibrillated structure.

EXAMPLE III

Filaments with a regularly structurized surface and having a diameter of $0.7 \times 10^{-4}$ m, a tensile strength of 0.65 GPa, a modulus of 8 GPa, a strength of a square knot of 0.45 GPa and an elongation at break of 19% were prepared by spinning poly(L-lactide) containing 5% by weight of polyester urethane from an 18 wt % solution in anhydrous trichlormethane. The poly(L-lactide) had a viscosity-average molecular weight of $4.0 \times 10^5$. The fibre was drawn at 150° C. to a draw ratio of 24. The poly(L-lactide)/polyester urethane monofilament so obtained has a highly fibrillated structure.

EXAMPLE IV

Highly fibrillated filaments having a diameter of $0.6 \times 10^{-4}$ m, a tensile strength at break of 0.7 GPa were kept in water at 37° C. for 10 to 200 days. After about 150 days the filaments were hydrolysed as to 50%. This rate of hydrolysis is comparable to that of PDS filaments of similar strength and thickness.

We claim:

1. A process for the manufacture for filament involving dry-spinning a spinning mixture comprising a polyester material and an additive, wherein the filament is prepared by dry-spinning, at room temperature, a solution in which the polyester material is poly(L-lactide), PLLA, poly (DL-lactide), PDLLA, or combinations thereof, in a concentration in the range of 5–70% by weight in the presence of the additive, the additive being a polyurethane which is a biodegradable polyester urethane material.

2. A process according to claim 1, wherein the concentration of the polylactide in the solution is in the range of 10–40% by weight.

3. A process according to claim 1, wherein $CHCL_3$, $CH_2Cl_2$) or both, is used as the solvent material in forming the solution.

4. A process according to claim 2, wherein $CHCL_3$, $CH_2Cl_2$, or both, is used as the solvent material in forming the solution.

5. A process according in claim 1, wherein the additive material used is soluble in $CHCl_3$, $CH_2Cl_2$, $C_2H_5OH$, or combinations thereof, and has a melt temperature in the range of 40°–180° C.

6. A process according to claim 2, wherein the additive material used is soluble in $CHCl_3$, $CH_2Cl_2$, $C_2H_5OH$, or combinations thereof, and has a melt temperature in the range of 40°–180° C.

7. A process according to claim 3, wherein the additive material used is soluble in $CHCl_3$, $CH_2Cl_2$, $C_2H_5OH$, or combinations thereof, and has a melt temperature in the range of 40°–180° C.

8. A process according to claim 1, wherein the concentration of the additive material in the polyester material is in the range of 1–45% by weight and the polyester material is a polylactide.

9. A process according to claim 2, wherein the concentration of the additive material in the polyester material is in the range of 1–45% by weight and the polyester material is a polylactide.

10. A process according to claim 3, wherein the concentration of the additive material in the polyester material is in the range of 1–45% by weight and the polyester material is a polylactide.

11. A process according to claim 1, wherein the concentration of the polylactide in the solution is in the range of 20% by weight.

* * * * *